United States Patent
Knoepfle et al.

(10) Patent No.: US 9,782,202 B2
(45) Date of Patent: Oct. 10, 2017

(54) SURGICAL DISTANCE ADJUSTING ASSEMBLY FOR A BONE DISTRACTOR

(71) Applicant: Stryker European Holdings I, LLC, Kalamazoo, MI (US)

(72) Inventors: Christian Knoepfle, Donaueschingen (DE); Karl Greiner, Muehlheim (DE); Manfred Schmuck, Muehlheim-Stetten/Donau (DE); Michael Volk, Waldshut-Tiengen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 451 days.

(21) Appl. No.: 14/103,252

(22) Filed: Dec. 11, 2013

(65) Prior Publication Data

US 2014/0163576 A1    Jun. 12, 2014

(30) Foreign Application Priority Data

Dec. 12, 2012    (EP) .................................... 12008294

(51) Int. Cl.
*A61B 17/66* (2006.01)
*A61B 17/80* (2006.01)
*A61B 17/00* (2006.01)

(52) U.S. Cl.
CPC ............ *A61B 17/66* (2013.01); *A61B 17/663* (2013.01); *A61B 17/666* (2013.01); *A61B 17/8071* (2013.01); *A61B 2017/00991* (2013.01)

(58) Field of Classification Search
CPC ...... A61B 17/66; A61B 17/663; A61B 17/666
USPC ......................................... 606/105, 280–299
See application file for complete search history.

(56) References Cited

U.S. PATENT DOCUMENTS

| | | | |
|---|---|---|---|
| 5,672,177 A | * | 9/1997 | Seldin ................ A61B 17/8009 606/105 |
| 5,855,580 A | | 1/1999 | Kreidler et al. |
| 5,895,387 A | | 4/1999 | Guerrero et al. |
| 5,902,304 A | | 5/1999 | Walker et al. |
| 6,113,599 A | | 9/2000 | Landsberger |
| 6,203,548 B1 | | 3/2001 | Helland |
| 6,277,124 B1 | | 8/2001 | Haag |
| 6,423,069 B1 | | 7/2002 | Sellers |

(Continued)

FOREIGN PATENT DOCUMENTS

| | | |
|---|---|---|
| DE | 19537023 A1 | 4/1996 |
| DE | 298 13 087 U1 | 12/1998 |

(Continued)

*Primary Examiner* — Christopher Beccia
(74) *Attorney, Agent, or Firm* — Lerner, David, Littenberg, Krumholz & Mentlik, LLP

(57) ABSTRACT

A surgical distance adjusting assembly for a distractor has a base having a first connecting portion configured to hold a first bone attachment member and a carrier having a second connecting portion configured to hold a second bone attachment member. The base and the carrier are movable relative to each other, wherein the first and second connecting portions provide a releasable mechanical coupling to the first and second bone attachment members. The releasable mechanical coupling comprises a hook member at one or both of the first and second connecting portions and configured to engage the respective bone attachment member. Alternatively, the releasable mechanical coupling comprises an opening at one or both of the first and second connecting portions. The opening has a thread for a fixation screw configured to releasable couple the respective bone attachment member to the respective connecting portion.

20 Claims, 13 Drawing Sheets

(56) References Cited

U.S. PATENT DOCUMENTS

| | | |
|---|---|---|
| 6,471,706 B1 | 10/2002 | Schumacher et al. |
| 6,752,808 B2 | 6/2004 | Schumacher |
| 6,786,910 B2 | 9/2004 | Cohen et al. |
| 6,884,243 B2 * | 4/2005 | Sellers ................. A61B 17/663 606/105 |
| 6,908,469 B2 | 6/2005 | Sellers et al. |
| 7,252,668 B2 | 8/2007 | Wolgen |
| 7,771,427 B2 | 8/2010 | Cohen et al. |
| 7,771,434 B2 | 8/2010 | Johnston |
| 2005/0002134 A1 | 1/2005 | Ohtake et al. |
| 2005/0149023 A1 * | 7/2005 | Ritland .............. A61B 17/7007 403/377 |
| 2006/0079902 A1 * | 4/2006 | Johnston ............. A61B 17/663 606/71 |
| 2011/0125162 A1 * | 5/2011 | Noon ................... A61B 17/663 606/105 |

FOREIGN PATENT DOCUMENTS

| | | |
|---|---|---|
| DE | 20008797 U1 | 8/2000 |
| EP | 1162919 A1 | 12/2001 |
| EP | 2229901 A1 | 9/2010 |
| WO | 9720512 | 6/1997 |
| WO | 9902097 A1 | 1/1999 |
| WO | 0056235 A1 | 9/2000 |
| WO | 01/30249 | 5/2001 |
| WO | 0178612 A1 | 10/2001 |
| WO | 2006023870 A2 | 3/2006 |
| WO | 2011038209 A2 | 3/2011 |
| WO | 2012145454 A1 | 10/2012 |

\* cited by examiner

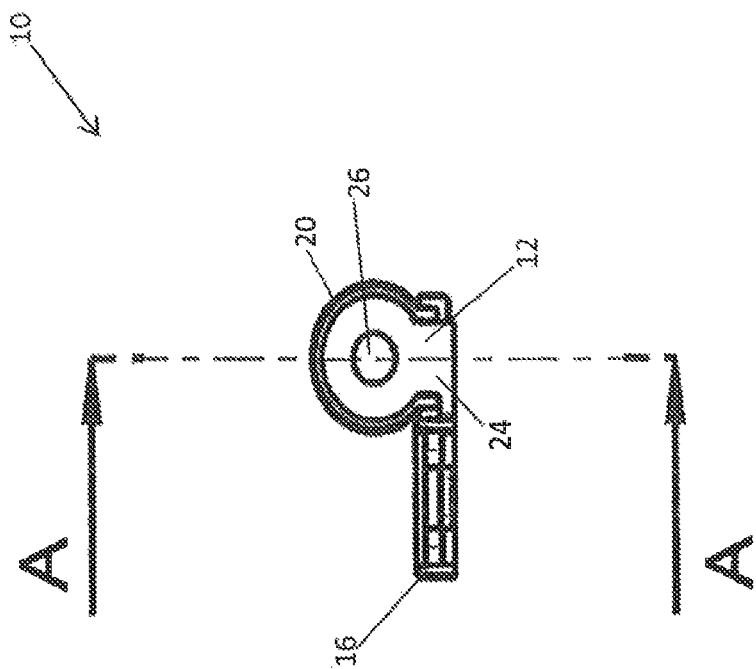
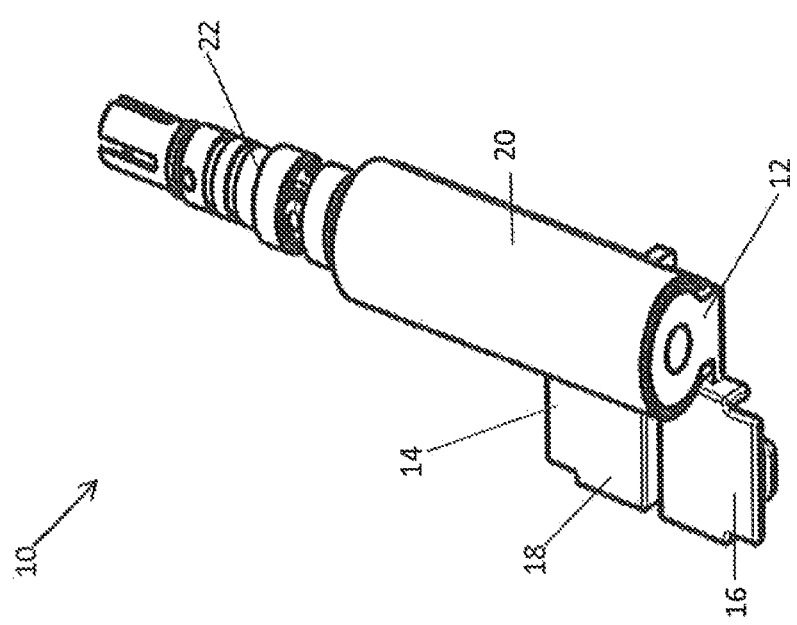

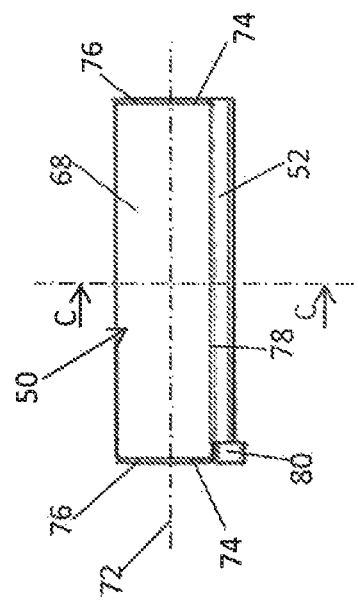
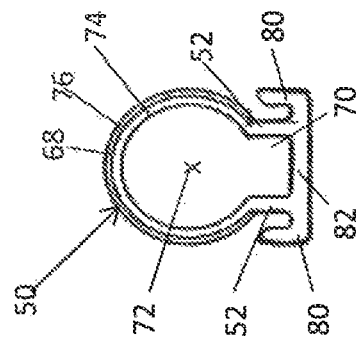
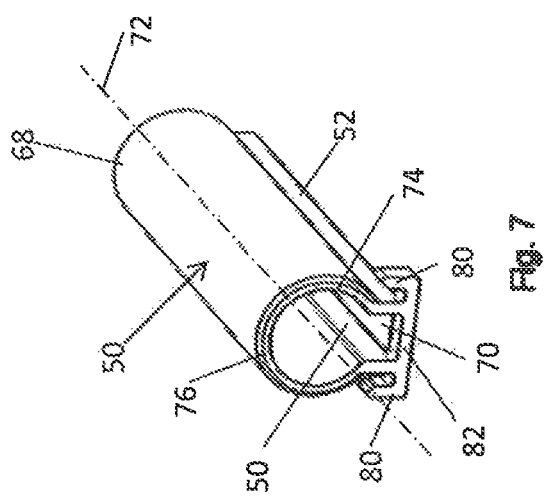
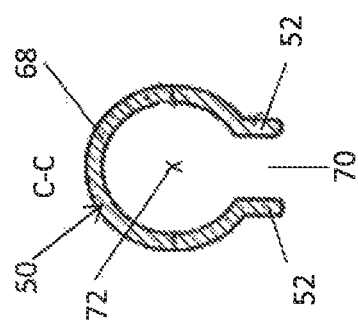

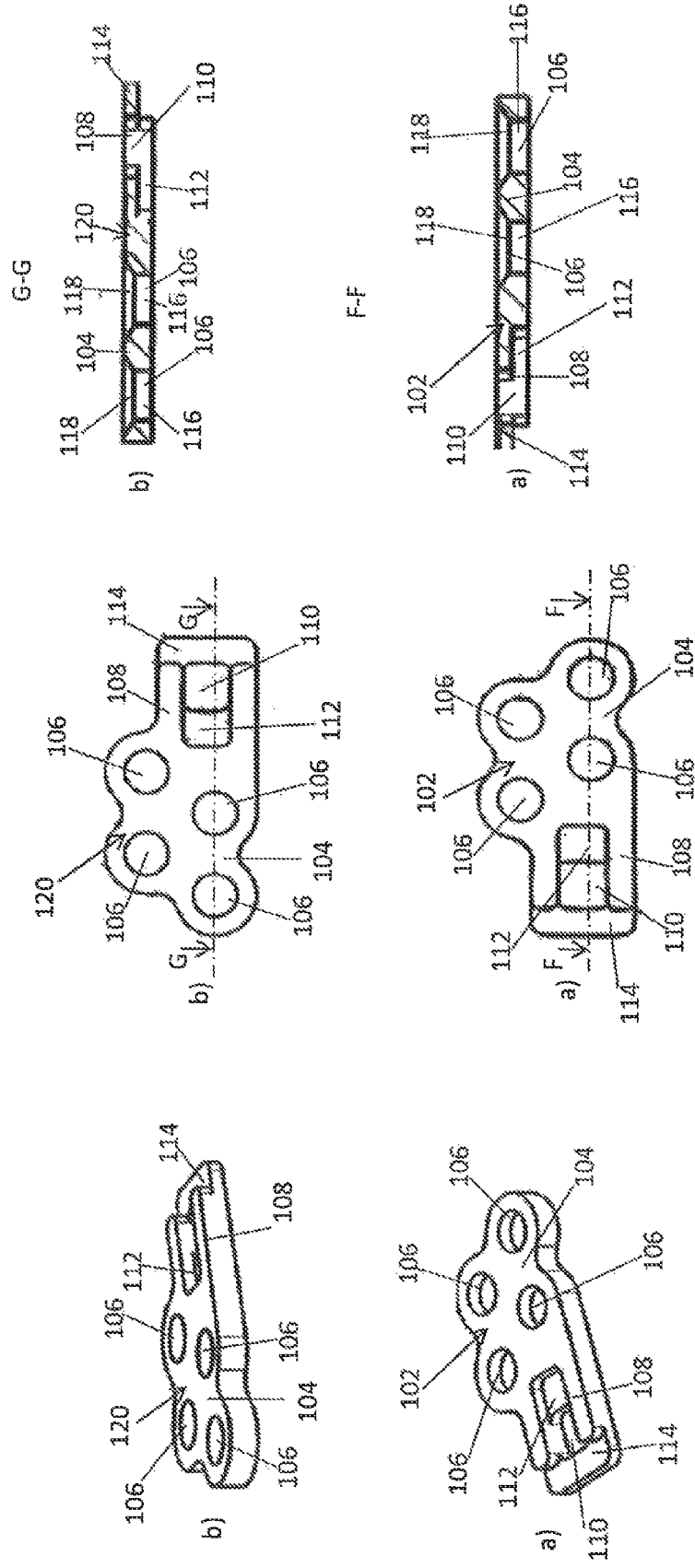

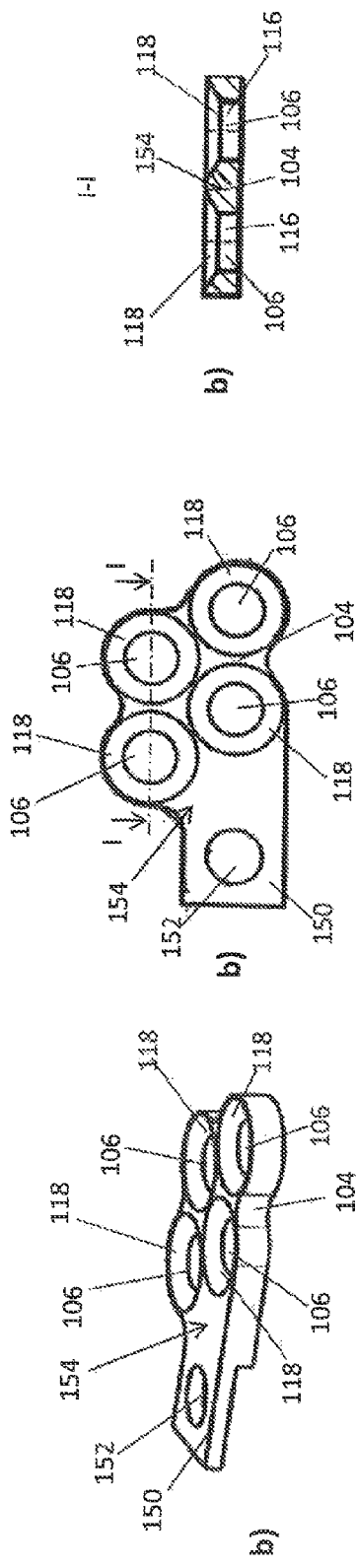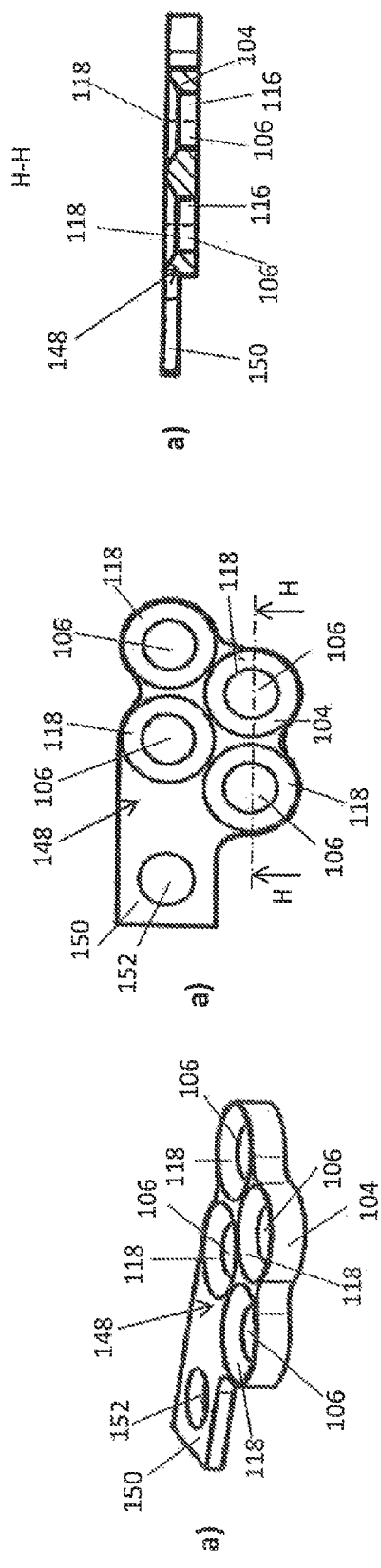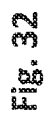

SURGICAL DISTANCE ADJUSTING ASSEMBLY FOR A BONE DISTRACTOR

CROSS-REFERENCE TO RELATED APPLICATIONS

The present application claims priority to European Patent Application No. 12008294.6 filed Dec. 12, 2012, the disclosure of which is hereby incorporated herein by reference.

BACKGROUND OF THE INVENTION

The present disclosure generally relates to a surgical distance adjusting assembly for use in surgical procedures. In particular, a surgical distance adjusting assembly for a bone distractor, the bone distractor as well as a system comprising the bone distractor are described.

When performing a reconstructive osteotomy or segment advancement of a cranium or jaw bone, the bone is typically separated into two or more sections. Plates of a bone distractor are then fixed to the respective bone sections by bone screws.

After their fixation to bone, the plates are successively distracted. The bone distractor may be operated by rotating a wire through an incision in the skin of the patient. The successive separation of the bone sections causes new bone to form in the generated gap, whereby the bone is gradually lengthened. During the formation of new bone in the gap, the distractor maintains a fixed gap width.

U.S. Pat. No. 6,908,469 discloses a maxillary bone distractor comprising a lead screw having an external thread in engagement with an internal thread of an inner sleeve. The distal end of the inner sleeve is fixed to a distal plate. The lead screw is journaled within an outer sleeve having an external thread to which a proximal plate is coupled. The outer sleeve is rotationally fixed relative to the inner sleeve.

After the distraction operation and a consolidation phase, the entire bone distractor (including the plates) has to be explanted, since the plates are fixed to the bone distractor. Thus, two significant invasive surgical procedures, namely one to implant the bone distractor device and another to remove it after the consolidation phase of bone, are necessary.

U.S. Pat. No. 6,423,069 discloses an orthopedic system comprising two plates each having a faster-connecting portion. The proximal plate is coupled to a proximal fastener by a detent mechanism, wherein a depression is provided on the proximal plate and an arm with a projection complementary to the shape of the depression is provided on the proximal fastener. When an outer sleeve is threaded into a bore of the proximal fastener, the arm projects out of the fastener into the depression of the proximal plate. Thus, the arm holds the proximal plate in position and prevents disengagement of the detent mechanism even when subjected to substantial forces such as those generated during the removal of the orthopedic device. The distal plate has a fastener-connecting portion generating a slip lock between a distal fastener and the distal plate. An inner sleeve is connected with its distal end to a bore of the distal fastener.

After the distraction operation and a consolidation phase, the device is removed by rotating the bone distractor to cause the distal fastener to disengage from the distal plate. Then, the outer sleeve has to be unthreaded from the proximal fastener to allow the arm to flex, such that when the device is pushed towards the bone surface, the detent mechanism holding the proximal fastener to the corresponding proximal footplate is released.

Although the orthopedic system of U.S. Pat. No. 6,423,069 is intended to provide a device that does not require a second surgical procedure to remove the device after the orthopedic procedure is completed, the system of U.S. Pat. No. 6,423,069 has several drawbacks. The orthopedic system has a bulky and very complicated structure which does not efficiently utilize its size. Further, due to the complicated removal mechanism, several steps are necessary to remove the bone distractor, wherein the sleeves, the fasteners and the plates may get stuck or jammed during explantation. The large size of the distractor and the complicated bone plate holding and removal mechanism also lead to more interference with surrounding tissue, with an increased risk of infections.

U.S. Pat. No. 5,895,387 discloses a distractor for craniofacial bone distraction. The bone distractor has first and second clamps are slideably connected via rods. The rods are connected to the first clamp and extend through holes in the second clamp. The second clamp includes a threaded hole through which extends a threaded rod. The threaded rod has an end engaging an anvil area of the first clamp. Further, each clamp includes holes for receiving bone pins or bone screws to directly attach the clamps to bone. As threaded rod is turned, an expansion force is generated between the first and second clamp. Thus, similar to the distractor of U.S. Pat. No. 6,908,469, two invasive surgical procedures, namely one to implant the bone distractor and another to remove it after the consolidation phase of bone, are necessary.

U.S. Pat. No. 7,771,434 B2 discloses a bone distractor having a threaded rod rotatably disposed within an elongated tubular housing. The elongated housing is provided with an axial slot, wherein a proximal plate-mounting means is in communication with the threaded rod such that rotation of the threaded rod results in movement of the proximal plate-mounting means in the proximal axial direction. Further, a distal plate-mounting means is affixed to the distal end of the housing. The distal and proximal plate-mounting means comprise U-shaped brackets for receiving bone plates. The bone plates are secured to the brackets and to the bone segments by bone screws inserted through apertures in the brackets and in the bone plates.

BRIEF SUMMARY OF THE INVENTION

Accordingly, there is a need for a surgical distance adjusting assembly for a bone distractor facilitating the associated surgical procedure, in particular upon explantation of the bone distractor.

A surgical distance adjusting assembly for a bone distractor is provided, wherein the assembly comprises a base having a first connecting portion configured to hold a first bone attachment member, and a carrier having a second connecting portion configured to hold a second bone attachment member. The base and the carrier are movable relative to each other and the first and second connecting portions provide a releasable mechanical coupling to the first and second bone attachment members. Further, the releasable mechanical coupling comprises a hook member at one or both of the first and second connecting portions to engage the respective bone attachment member.

In the aspect described above, the first and second connecting portions may comprise an engagement surface configured to slidably abut against the respective bone attachment member. The engagement surface may delimit an at least partially closed engagement cavity of the respective bone connecting portion. As an example, the engagement surface may delimit a bottom the engagement cavity. The engagement cavity may comprise one or more sidewalls for guiding a sliding movement of the bone attachment member to be at least partially accommodated therein.

Each of the first and second connecting portions may comprise one or more hook members configured to releasable engage an engagement portion of the respective bone attachment member. As an example, one (e.g., a single) hook member is arranged within the respective engagement cavity. Alternatively, several, e.g., two, three or more hook members may be arranged within the respective engagement cavity. Further, each hook member may be pointing in a direction of a longitudinal axis of the surgical distance adjusting assembly. Each engagement cavity having a hook member positioned therein thus provides a releasable mechanical coupling to the respective bone attachment members. Further, the hook member may be integrally with the respective connecting portion.

According to a further aspect, there is provided a surgical distance adjusting assembly for a bone distractor is provided, wherein the assembly comprises a base having a first connecting portion configured to hold a first bone attachment member, and a carrier having a second connecting portion configured to hold a second bone attachment member. The base and the carrier are movable relative to each other and the first and second connecting portions provide a releasable mechanical coupling to the first and second bone attachment members. Further, the releasable mechanical coupling comprises an opening at one or both of the first and second connecting portions, the opening having a thread for a fixation screw configured to releasably couple the respective bone attachment member to the respective connecting portion.

One or both of the first and second connecting portions may comprise a recess configured to slidably receive the respective bone attachment members. Alternatively, the respective connecting portion may be formed in a fully planar fashion.

In one implementation, each of the first and second connecting portions may include the threaded opening. In addition, or alternatively, more than one threaded opening may be provided per connecting portion.

The opening may be formed as an elongated or circular through hole. Further, the opening may penetrate the recess, if present. The respective opening may penetrate the first and/or second connecting portion(s) and the optional recess(es) in a direction substantially perpendicular to a longitudinal axis of the surgical distance adjusting assembly. In this case, the respective bone attachment member may have an opening (e.g., an elongated or circular through hole) which coincides with the respective connecting portion, when the respective bone attachment member is coupled to the respective connecting portion. Thus, a fixation screw may penetrate the opening of the respective connecting portion and the opening of the corresponding bone attachment member.

The fixation screw can be a fastener, e.g., a screw or peg having a thread. Each opening may have an internal thread which mates with an external thread of the fixation screw. The thread of the opening can be a machine thread. The fixation screw can be formed as machine screws, i.e., a screw having a machine thread. The threads of each fixation screws may be configured to matingly engage the threads of each opening.

In the aspects described above, the recess or the engagement cavity may have a substantially cuboidic shape. Other shapes (e.g., of a trapezoidal cross-section) are also possible. The recess or the engagement cavity may be adapted to the shape of an assembly connecting portion of the respective bone attachment member to provide a substantially matching fit therebetween.

The engagement cavity or the recess may open out in a direction of a longitudinal axis of the surgical distance adjusting assembly. The engagement cavity or the recess may open out in opposite directions along a direction of the longitudinal axis of the surgical distance adjusting assembly. As an example, the engagement cavity or the recess of the first connecting portion may open out towards a first end of the surgical distance adjusting assembly, and the engagement cavity or the recess of the second connecting portion may open out towards a second end of the surgical distance adjusting assembly. Alternatively, or in addition, the engagement cavity or the recess may open out in a direction substantially perpendicular to a longitudinal axis of the surgical distance adjusting assembly. Further, each engagement cavity or recess can be formed as a slit or a shoe configured to slidaby receive a corresponding assembly connecting portion of the respective bone attachment member.

The surgical distance adjusting assembly can be configured to release, upon a movement of the carrier and the base towards each other in a direction of a longitudinal axis of the surgical distance adjusting assembly, the first and the second bone attachment members from the first and second connecting portions. The carrier and the base may be configured as moving in opposite directions to each other.

The carrier may be rotationally locked relative to the base. This can be achieved by a guiding structure or guiding mechanism that is stationary relative to the base and extends substantially in the longitudinal direction of the assembly. The guiding structure or guiding mechanism may be engaged with the carrier or with the part rotationally fixed to the carrier.

The surgical distance adjusting assembly may further comprise a rod having an external thread, wherein the rod is coupled to the base, and a sleeve having an external thread and an internal thread for engaging the thread of the rod. The rod may be directly coupled to the base, or via one or more intermediate elements. The base may comprise a surface and the rod may be fixed to the base substantially perpendicular to that surface. The coupling of the rod to the base may prevent a rotation of the rod relative to the base. The rod may thus be rigidly fixed relative to the base. For example, the rod may be threadingly engaged with the base. Alternatively, or in addition, the rod may be adhered to the base. As a further alternative, the rod and the base may be machined in one single piece. Thus, the rod and the base may be formed integrally. The external thread of the rod may extend along the entire length of the rod. Alternatively, the thread of the rod may only extend along a portion of the rod (e.g., a portion not in contact with the base).

The carrier may have an internal thread for engaging the external thread of the sleeve. Further, the carrier may comprise a cylindrical portion with a through hole. The internal thread of the carrier may be approximately concentric with the through hole. Thus, the through hole may include the internal thread.

The surgical distance adjusting assembly may further comprise a sleeve cover having an axially extending aperture for guiding the carrier. The sleeve cover may be rotationally locked with respect to the base. Moreover, the sleeve cover may substantially extend along the entire length of the sleeve. A radial clearance for accommodating the carrier may be established between the sleeve and the sleeve cover. This radial clearance may also accommodate a rod cover.

The internal thread and external thread of the sleeve may have the same longitudinal extension. These threads may extend along the entire length of the sleeve.

The assembly may be configured so that the carrier is closest to the base when the sleeve is closest to the base (i.e., in the most reduced configuration of the assembly). Further, when the carrier reaches the end of the external thread of the sleeve opposite to the base (i.e., in the most distracted configuration of the assembly), the internal thread of the sleeve may be engaged with less than the half of the external thread of the rod. For example, the sleeve may in this configuration be engaged with 30%, 20% or less of the thread of the rod.

The sleeve cover may have a cross section in the shape of a circular portion of at least 180, 190 or 200 degrees and two parallel flanges extending from each end of the circular portion. The ends of the sleeve and the sleeve cover facing the base may be aligned in a plane perpendicular to the longitudinal axis of the assembly.

The base of the surgical distance adjusting assembly may comprise a rod cover. The rod cover may comprise an axially extending aperture (e.g., substantially parallel with its longitudinal axis) in which the carrier is movable. Boundaries of the aperture may rotationally lock the carrier relative to the base. The rod cover may substantially extend along the entire length of the rod. A radial clearance for accommodating the sleeve cover, the carrier and the sleeve may be established between the rod and the rod cover.

The rod and the sleeve may be arranged in a telescopic arrangement. Thus, the sleeve cover and the rod cover may be arranged in a telescopic arrangement as well. The sleeve cover may be slidably accommodated within the rod cover. Alternatively, the rod cover may be slidably accommodated within the sleeve cover.

The end of the rod cover opposite to the base may be aligned with the end of the external thread of the sleeve opposite to the base in a plane perpendicular to the longitudinal axis of the assembly, when the sleeve abuts against the base.

By rotation of the sleeve, the base and the carrier may be configured as moving in opposite directions in relation to the sleeve along a longitudinal axis of the sleeve. The external thread of the rod and external thread of the sleeve may have different handedness. Alternatively, or in addition, the external thread of the rod and the external thread of the sleeve may have the same or a different pitch. This pitch may be between 0.2 mm and 2.0 mm. For example, this pitch can be 0.5 mm.

According to a further aspect, there is provided a bone distractor comprising an assembly as generally described above and hereinafter, the first bone attachment member and the second bone attachment member. The first bone attachment member is releasably coupled to the first connecting portion of the base and the second bone attachment member is releasably coupled to the second connecting portion of the carrier.

The first and second bone attachment members may be bone plates. Each of the attachment members may comprise one or more attachment openings configured to receive a bone fastener for attaching the attachment member to a bone.

The first and second bone attachment members may be made of a resorbable material. Optionally, one or more (or all) components of the surgical distance adjusting assembly may be made of a resorbable material.

The bone distractor may further comprise one or more fixation screws for releasably coupling at least one of the first and second bone attachment members to the respective connecting portion, wherein each fixation screw is configured to matingly engage the respective opening. Alternatively, or in addition, the opening may have an internal thread which mates with the external thread of the associated fixation screw.

According to a further aspect, there is provided a system comprising the bone distractor as generally described above and hereinafter, wherein the system further comprises bone fasteners for attaching the first bone attachment member and the second bone attachment member to bone.

The bone fasteners may be bone screws, bone pegs, wire-like fasteners or the like. The bone fasteners may be made of a resorbable material.

BRIEF DESCRIPTION OF THE DRAWINGS

Further details, advantages and aspects of the present disclosure will become apparent from the following embodiments taken in conjunction with the drawings wherein:

FIG. 1 shows a perspective view of a surgical distance adjusting assembly ac-cording to a first embodiment in its most reduced configuration;

FIG. 2 shows a rear view of the adjusting assembly of FIG. 1;

FIG. 7 shows a perspective view of a sleeve cover;

FIG. 8 shows a side view of the sleeve cover of FIG. 7;

FIG. 9 shows a cross section of the sleeve cover along line C-C of FIG. 8;

FIG. 10 shows a rear view of the sleeve cover of FIG. 7;

FIG. 17*a* shows a perspective view of a first bone attachment member according to a first embodiment;

FIG. 17*b* shows a perspective view of a second bone attachment member according to a first embodiment;

FIG. 18*a* shows a bottom view of the first bone attachment member of FIG. 17*a*;

FIG. 18*b* shows a bottom view of the second bone attachment member of FIG. 17*b*;

FIG. 19*a* shows a cross section of the first bone attachment member along line F-F of FIG. 18*a*;

FIG. 19*b* shows a cross section of the second bone attachment member along line G-G of FIG. 18*b*;

FIG. 30a shows a perspective view of a first bone attachment member according to a second embodiment;

FIG. 30b shows a perspective view of a second bone attachment member according to a second embodiment;

FIG. 31a shows a top view of the first bone attachment member of FIG. 30a;

FIG. 31b shows a top view of the second bone attachment member of FIG. 30b;

FIG. 32a shows a cross section of the first bone attachment member along line I-I of FIG. 31a;

FIG. 32b shows a cross section of the second bone attachment member along line J-J of FIG. 31b.

DETAILED DESCRIPTION

Figure 3:
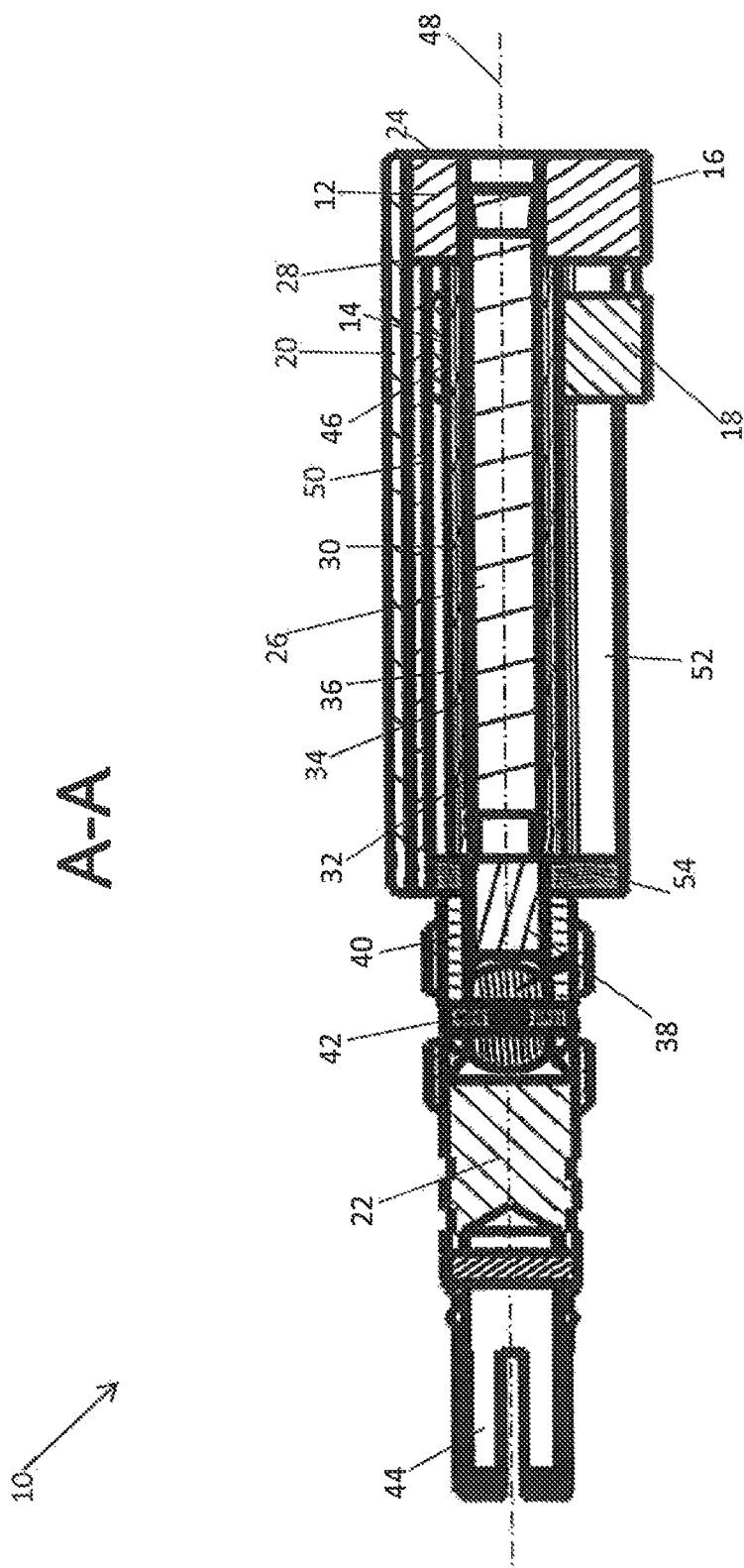
FIG. 3 shows a cross section of the adjusting assembly along line A-A of FIG. 2.

In the following, embodiments of a surgical distance adjusting assembly for a bone distractor will be described. The same reference numerals will be used to denote the same or similar structural features. The surgical distance adjusting assembly is referred to as a bone distractor when it comprises bone attachment members. The bone distractor described herein is particularly suited for being implanted in the mandibular region.

FIG. 1 shows a perspective view of an embodiment of a surgical distance adjusting assembly 10. In this view, the surgical distance adjusting assembly 10 is in its most reduced configuration. The surgical distance adjusting assembly 10 is now referred to as an adjusting assembly 10. The adjusting assembly 10 comprises a base 12 and a carrier 14. The base 12 has a first connecting portion 16 configured to hold a first bone attachment member (not shown in FIG. 1). The carrier 14 has a second connecting portion 18 configured to hold a second bone attachment member (not shown in FIG. 1). Further, the adjusting assembly 10 comprises a rod cover 20 and a rotation transmitting member 22.

FIG. 2 shows a rear view of the adjusting assembly 10 of FIG. 1. Here, the base 12 comprising the rod cover 20 and the first connecting portion 16 can be seen. The base 12 has a flat outer surface 24 and a central portion with a cylindrical clearance. A rod 26 is rigidly fixed to the base 12 at the central portion within the cylindrical clearance.

FIG. 3 shows a cross section of the adjusting assembly 10 along line A-A of FIG. 2. The adjusting assembly 10 is here again in its most reduced configuration. Apart from the flat outer surface 24, the base 12 further comprises a flat inner surface 28. The rod 26 is fixed to the base 12 perpendicular to this flat inner surface 28.

The rod 26 has an external thread 30. The external thread 30 extends from the flat inner surface 28 of the base 12 almost to the end of the rod 26 opposite to the base 12. In other realizations, the external thread 30 may extend from the flat inner surface 28 of the base 12 all the way to the end of the rod 26 not connected to the base 12, i.e., to the opposite side of the base 12.

The adjusting assembly 10 further comprises a sleeve 32 having an internal thread 34. The internal thread 34 of the sleeve 32 is threadingly engaged with the external thread 30 of the rod 26. In the position illustrated in FIG. 3, the sleeve 32 abuts against the flat inner surface 28 of the base 12.

The sleeve 32 further comprises an external thread 36. The internal thread 34 and the external thread 36 extend along the same length of the sleeve 32. The external thread 36 of the sleeve 32 and the external thread 30 of the rod 26 may have different handedness.

At one end of the sleeve 32, opposite to the base 12, a protrusion 38 is provided that is rigidly fixed to the sleeve 32. The protrusion 38 is connected to a connection member 40 of the rotation transmitting member 22. The connection member 40, the protrusion 38 and the sleeve 32 together establish a circumferential groove. A Hooke's joint and a tool interface 44 are provided on the rotation transmitting member 22.

The carrier 14 comprising the second connecting portion 18 can further be seen in FIG. 3. The carrier 14 comprises an internal thread 46 engaged with the external thread 36 of the sleeve 32.

The dimensions of the carrier 14 and the base 12 are exaggerated. For example, these components can be made substantially shorter along a longitudinal axis 48 of the adjusting assembly 10 as depicted in FIG. 3. The width of the carrier 14 is approximately equal to the width of the base 12 along the longitudinal axis 48.

The adjusting assembly 10 further comprises a sleeve cover 50. The sleeve cover 50 extends along the entire length of the sleeve 32 and also circumferentially encloses a part of the protrusion 38. In the illustrated position of FIG. 3, the sleeve cover 50 abuts against the inner surface 28 of the base 12. A radial clearance accommodating the carrier 14 is established between the sleeve 32 and the sleeve cover 50. Reference numeral 52 indicates one of two parallel flanges of the sleeve cover 50.

The sleeve cover 50 comprises a stop portion 54 for limiting a relative axial movement between the sleeve 32 and the sleeve cover 50. Further, the stop portion 54 limits a relative axial movement between the sleeve 32 and the carrier 14. The stop portion 54 extends in a plane perpendicular to the longitudinal axis 48. In the present embodiment, the stop portion 54 is realized in the form of a wall closing a front face of the sleeve cover 50 opposite to the base 12.

A through hole is arranged in the stop portion 54 in which the protrusion 38 of the sleeve 32 is received. The stop portion 54 is engaged in the circumferential groove established by the connecting member 40, the protrusion 38 and the sleeve 32. Thereby, the sleeve 32 is rotatable within the sleeve cover 50. Further, the sleeve cover 50 is longitudinally engaged with the sleeve 32.

The rod 26 and the sleeve 32 are arranged in a telescopic arrangement. In the same manner, the sleeve cover 50 and the rod cover 20 are arranged in a telescopic arrangement as will be discussed in more detail below. The rod cover 20 overlaps the rod 26 along the entire length of the rod 26. A radial clearance accommodating the sleeve cover 50 is established between the rod 26 and the rod cover 20. The sleeve cover 50 and the rod cover 20 are locked against relative rotation as will be described later in more detail. As can be seen in FIG. 3, the end of the rod cover 20 opposite to the base 12 is approximately aligned with the end of the sleeve cover 50 and the stop portion 54 in a plane perpendicular to the longitudinal axis 48 of the adjusting assembly 10, when the adjusting assembly 10 is in its most reduced configuration.

The carrier 14 is slidingly accommodated in the sleeve cover 50 and the rod cover 20. Moreover, the carrier 14 partially extends through apertures in the sleeve cover 50 and the rod cover 20 as will be described later in more detail. Thereby, the carrier 14 is rotationally locked relative to the sleeve cover 50 and the rod cover 20.

By rotating the tool interface 44, the sleeve 32 is correspondingly rotated via the rotation transmitting member 22, the Hookes' joint 42, the connection member 40 and the protrusion 38. The sleeve 32 thereby moves along the longitudinal axis 48 relative to the rod 28 away from the base 12.

Upon rotation of the sleeve 32, the carrier 14 rotationally locked relative to the sleeve cover 50 also moves along the longitudinal axis 48 relative to the sleeve 32 away from the base 12. For one given rotational speed of the sleeve 32, the carrier 14 moves faster relative to the rod 26 than the sleeve 32 moves relative to the rod 26 along the longitudinal axis 48.

Figure 4:
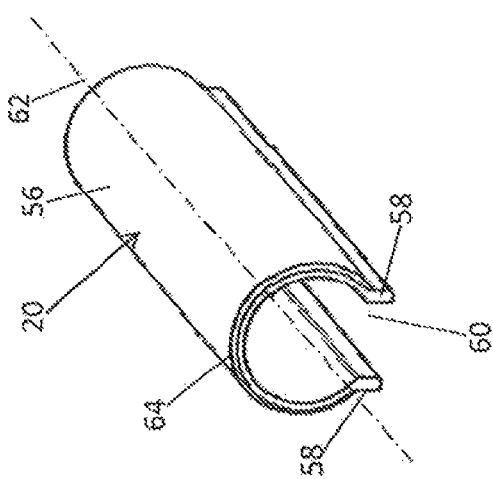
FIG. 4 shows a perspective view of a rod cover.

FIG. 4 shows a perspective view of the rod cover 20. The rod cover 20 can be attached to the base 12 as previously described. The rod cover 20 comprises a cylindrical portion 56 and two flanges 58. The cylindrical portion 56 and the two flanges 58 of the rod cover 20 are formed of one sheet of material, e.g., metal. Between the flanges 58, an aperture 60 is provided, extending along the cylindrical portion 56 of the rod cover 20. Reference numeral 62 indicates a longitudinal axis of the rod cover 20. The longitudinal axis 62 is concentric with the cylindrical portion 56. The rod cover 20 is further provided with a chamfered portion 64 at each end thereof as shown in FIGS. 4 and 5.

Figure 5:
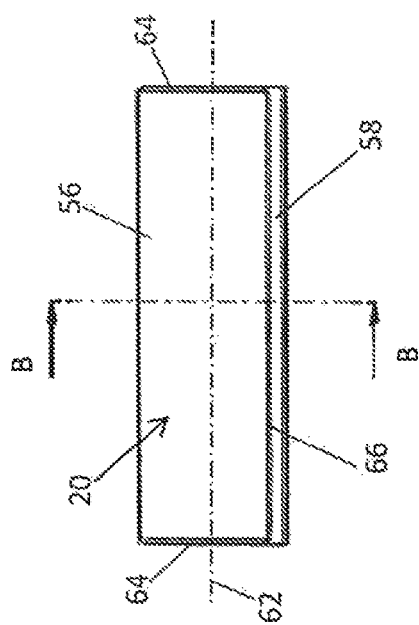
FIG. 5 shows a side view of the rod cover of FIG. 4.

FIG. 5 shows a side view of the rod cover 20. In this illustration, it can be seen that the lower end of the flange 58 is parallel to the axis 62 of the rod cover 20. A chamfered portion 66 is provided between the cylindrical portion 56 and the flange 58.

Figure 6:
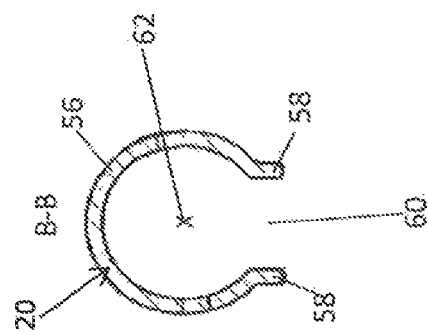
FIG. 6 shows a cross section of the rod cover along line B-B of FIG. 5.

FIG. 6 shows a cross section of the rod cover 20 along line B-B of FIG. 5. Here, it can be seen that the cylindrical portion 56 has an angular extension of approximately 270 degrees about the longitudinal axis 62 of the rod cover 20. The flanges 58 are parallel (to each other) and extend in a vertical direction from the cylindrical portion 56.

FIG. 7 shows a perspective view of the sleeve cover 50. The sleeve cover 50, similar to the rod cover 20, comprises a cylindrical portion 68 and two flanges 52 extending vertically from the cylindrical portion 68. The two flanges 52 define an aperture 70 extending parallel with a longitudinal axis 72 of the sleeve cover 50 along the entire length of the sleeve cover 50. The longitudinal axis 72 is concentric with the cylindrical portion 68 of the sleeve cover 50.

FIG. 8 shows a side view of the sleeve cover 50 of FIG. 7. The sleeve cover 50 comprises two vertical end portions 74 which are perpendicular to the longitudinal axis 72. Between each of the vertical end portions 74 and the cylindrical portion 68, a chamfered portion 76 is provided. Similarly, a chamfered portion 78 is provided between the cylindrical portion 68 and each flange 52.

FIG. 9 shows a cross section of the sleeve cover 50 along line C-C of FIG. 8. Here, it can be seen that the flanges 52 of the sleeve cover 50 are slightly higher than the flanges 58 of the rod cover 20 (see FIG. 6). The shape of the outer surface of the sleeve cover 50 thereby corresponds to the shape of the inner surface of the rod cover 20 and permits a guided telescoping movement as illustrated in FIG. 3. Further, the cylindrical portion 68 of the sleeve cover 50 has an angular extension of approximately 270 degrees about the longitudinal axis 72 of the sleeve cover 50.

FIG. 10 shows a rear view of the sleeve cover 50 of FIG. 7. As illustrated in FIGS. 7 and 10, the sleeve cover 50 comprises two L-shaped protrusions 80 positioned at one end (here, the rear end) of the sleeve cover 50. In the present embodiment, the rear end of the sleeve cover 50 is closest to the base 12 (see, e.g., FIGS. 1 and 3). The L-shaped protrusions 80 extend perpendicularly and outwardly from the flanges 52. Further, the aperture 70 of the sleeve cover 50 is bridged by a bridge portion 82 which extends from one L-shaped protrusion to the other L-shaped protrusion 80 opposite thereof. The bridge portion 82 connects the two flanges 52 with each other. Thus, the L-shaped protrusions 80 and the bridge portion 82 form together a T-shaped portion with the flanges 52. The flanges 58 of the rod cover 20 can engage within the space provided between the L-shaped protrusions 80 and the flanges 52 of the sleeve cover 50 to provide a guiding function therebetween as illustrated in FIG. 2.

Figure 11:
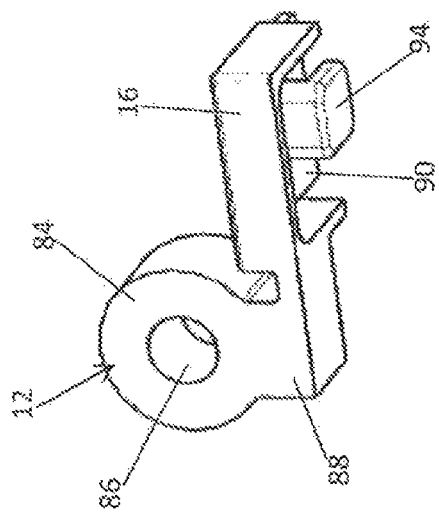
FIG. 11 shows a perspective view of a base according to a first embodiment.

FIG. 11 shows a perspective view of the base 12 according to a first embodiment. The base 12 comprises a cylindrical portion 84 with a cylindrical clearance 86. The rod 26 is thus rigidly fixed to the base 12 at the center of the cylindrical portion 84 within the cylindrical clearance 86. A cuboid 88 with a rectangular base extends radially from the cylindrical portion 84 of base 12. In FIG. 11, it can be seen that the outer contour of the cylindrical portion 84 of the base 12 corresponds to the inner surface of the rod cover 20 (see FIGS. 2 and 6).

Figure 12:
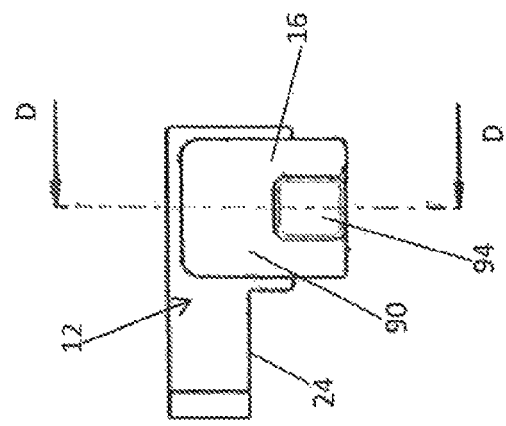
FIG. 12 shows a bottom view of the base of FIG. 11.

FIG. 12 shows a bottom view of the base 12 of FIG. 11. The base 12 comprises the first connecting portion 16 which substantially extends in a perpendicular direction with respect to a longitudinal axis of the cylindrical portion 84 of the base 12. Thus, the first connecting portion 16 of the base 12 substantially extends in a perpendicular direction with respect to the longitudinal axis 48 of the adjusting assembly 10 (see FIGS. 1 and 3). The base 12 and its first connecting portion 16 are formed from one single piece of material, e.g. metal. The first connecting portion 16 of the base 12 comprises an engagement cavity 90. The engagement cavity 90 is configured to slidably receive a bone attachment member (not shown in FIGS. 11 to 13). The engagement cavity 90 may have a substantially rectangular shape. The side walls of the engagement cavity 90 may thus be parallel with the longitudinal axis of the cylindrical portion 84 of the base 12 and therewith parallel with longitudinal axis 48 of the adjusting assembly 10. Alternatively, the engagement cavity 90 may have a substantially tapered shape, in which the side walls are tapered relative to the longitudinal axis of the cylindrical portion 84 of the base 12 (i.e., the side walls are tapered relative to the longitudinal axis 48 of the adjusting assembly 10).

Figure 13:
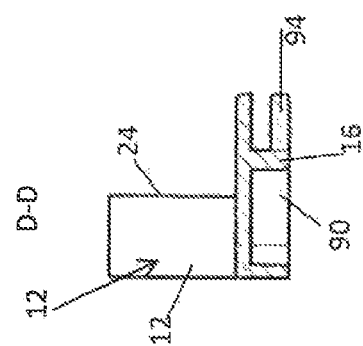
FIG. 13 shows a cross section of the base along line D-D of FIG. 12.

FIG. 13 shows a cross section of the base 12 along line D-D of FIG. 12. The engagement cavity 90 may have an U-shape. The U-shape of the engagement cavity 90 can be formed by a transverse plate at the front end of the base 12, wherein the transverse plate 92 bridges the side walls of the engagement cavity 90 (the transverse plate 92 is only shown in FIG. 21). The engagement cavity 90 substantially corresponds to the shape of an assembly connecting portion of the bone attachment members as will be described later in more detail. As shown in the FIGS. 11 to 13, the engagement cavity 90 of the first connecting portion 16 opens out in a direction of the longitudinal axis of the cylindrical portion 84 of the base 12. In this case, the engagement cavity 90 opens out in the direction of the longitudinal axis 48 of the adjusting assembly 10.

Further, the first connecting portion 16 comprises a hook member 94. The hook member 94 is configured to releasable engage on an engagement portion of the bone attachment members. Further, the hook member 94 is arranged within the engagement cavity 90. In the present embodiment, the hook member 94 is integrally with the first connecting portion 16 of the base 12. The hook member 94 has a substantially rectangular shape. In the present embodiment, the hook member 94 has a square shape. Other shapes, like circular, elliptical or triangular may also be possible. The hook member 94 also extends in a direction substantially parallel to the longitudinal axis of the cylindrical portion 84 of the base 12. Thus, the hook member 94 extends in a substantially parallel direction of longitudinal axis 48 of the adjusting assembly 10.

As shown in FIG. 12, the hook member 94 is arranged in the engagement cavity 90 in a central position. Further, the hook member 94 is substantially positioned at an outgoing end of the engagement cavity 90. In a cross-sectional view as illustrated in FIG. 13, the hook member 94 has, in the present embodiment, an L-shape. One leg of the L-shaped hook member 94 is substantially perpendicular to the inner bottom surface of the engagement cavity 90. The other leg of the L-shaped hook member 94 is substantially parallel to the inner bottom surface of the engagement cavity 90. Thus, this leg of the L-shaped hook member 94 is substantially parallel to the longitudinal axis 48 of the adjusting assembly 10. Other shapes, in cross-section, of the hook member 94 may also be possible, like an I- or V-shape.

Figure 14:
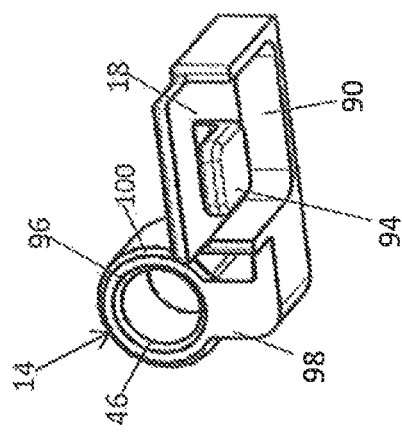
FIG. 14 shows a perspective view of a carrier according to a first embodiment.

FIG. 14 shows a perspective view of the carrier 14 according to a first embodiment. The carrier 14 comprises a cylindrical portion 96 in which the internal thread 46 is provided. A cuboid 98 with a rectangular base extends radially from the cylindrical portion 96. It can be seen in FIG. 14, that the outer contour of the carrier 14 (i.e., of its cylindrical portion 96) corresponds to the inner surface of the sleeve cover 50 (see FIGS. 3, 9 and 10). The cylindrical portion 96 has at its end portions in a longitudinal direction of the cylindrical portion 96 a chamfered portion 100. The chamfered portions 100 extend substantially along the outer circumference of the cylindrical portion 96.

Figure 16:
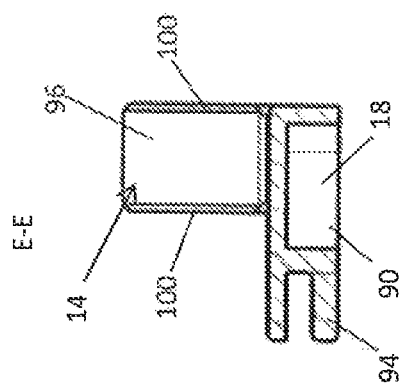
FIG. 16 shows a cross section of the carrier along line E-E of FIG. 14.
Figure 15:
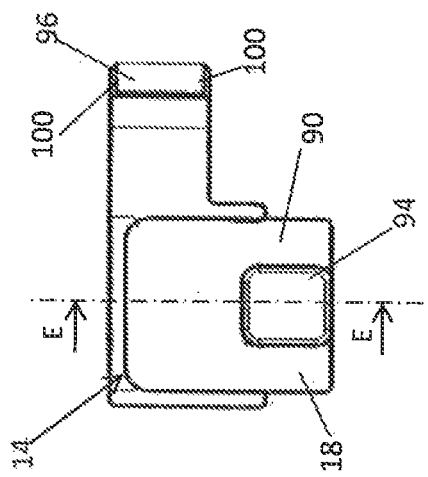
FIG. 15 shows a bottom view of the carrier of FIG. 14.

FIG. 15 shows a bottom view of the carrier 14 of FIG. 14 and FIG. 16 shows a cross section of the carrier 14 along line E-E of FIG. 15. As can be seen from FIGS. 14 to 16, the carrier 14 further comprises the second connecting portion 18. The second connecting portion 18 is configured to hold a second bone attachment member (not shown in FIGS. 14 to 16). The second connecting portion 18 provides a releasable mechanical coupling to the second bone attachment member. The second connecting portion 18 of the carrier 14 substantially corresponds to the first connecting portion 16 of base 12. Thus, the second connecting portion 18 includes the engagement cavity 90, the transverse plate 92 and the hook member 94 as generally described above with reference to FIGS. 11 to 13 and hereinafter.

FIG. 17a shows a perspective view of a first bone attachment member 102 according to a first embodiment. The first bone attachment member 102 may be in the form of a bone plate. The bone attachment member 102 may have several shapes which can be adapted as needed to the structure of the adjusting assembly 10 or to the bone structure. Thus, the first bone attachment member 102 may have an I-, T-, rectangular, triangular or palm shape. In the present embodiment as shown in FIG. 17a, the first bone attachment member 102 has a bone attachment portion 104 having an undulating outer periphery. The bone attachment portion 104 includes through holes 106. The through holes 106 may have a circular or elongated shape and will be described with reference to FIGS. 18a and 19a in more detail below. The first bone attachment member 102 further comprises an assembly connecting portion 108. The assembly connecting portion 108 has a substantially rectangular shape and is the counter-part of the first and second connecting portions 16 and 18 of the base 12 and the carrier 14 respectively.

FIG. 18a shows a bottom view of the first bone attachment member 102 of FIG. 17a. Here, it can be seen, that the assembly connecting portion 108 of the first bone attachment member 102 has a recess 110 in a central position of the assembly connecting portion 108. The recess 110 of the assembly connecting portion 108 has, in the present embodiment, a substantially square shape. Further, the recess 110 is configured to accommodate the hook member 94 of the base 12 or the carrier 14. The shape of the inner surface of the recess 110 thereby corresponds to the shape of the outer surface of the hook member 94 to provide an optimal insertion of the hook member 94 through the recess 110. The recess 110 may have another shape (e.g., rectangular, square, circular, elliptical, triangular, etc.) which corresponds to the shape of the hook member 94 as described above. The assembly connecting portion 108 further comprises an engagement portion 112 on which the hook member 94 can releasable engage. The engagement portion 112 may have the form of a cavity having an inner surface with a shape that substantially corresponds to the shape of the outer surface of the hook member 94. The side walls of the engagement portion 112 allow a guided movement of the hook member 94 in a direction of a longitudinal axis of the first bone attachment member 102, and therewith along a direction of the longitudinal axis of the cylindrical portion 84 or 96 of the base 12 and the carrier 14 respectively. Thus, the engagement portion 112 of the first bone attachment member 102 provides a guided movement of the hook member 94 in a direction of the longitudinal axis 48 of the adjusting assembly 10.

FIG. 19a shows a cross section of the first bone attachment member 102 along line F-F of FIG. 18a. Here, it can be seen that the recess 110 and the engagement portion 112 together have a L-shape for matingly accommodate the hook member 94. Further, the assembly connecting portion 108 of the first bone attachment member 102 has a step portion 114 at its outer end in the longitudinal direction of the first bone attachment member 102. The step portion 114 can be received by the engagement cavity 90, such that it is accommodated within the space defined by the engagement cavity 90 and the transverse plate 92, like a foot-shoe-mechanism.

As shown in FIGS. 17a to 19a, each through hole 106 has a circular shape. Alternatively, elongated through holes may be provided in the first bone attachment member 102. As shown in FIG. 19a, each through hole 106 has a cylindrical lower portion 116 and a countersink upper portion 118. The cylindrical lower portion 116 is at a bone contacting side of the first bone attachment member 102 and the countersink upper portion 118 is on a side opposite to the bone contacting side. The through holes 106 are adapted to receive bone fasteners (not shown in FIGS. 17a to 19a) for connecting the first bone attachment member 102 to bone. The bone fasteners may be bone screws, bone pegs or the like. The cylindrical lower portion 116 can be unthreaded or threaded. Thus, the cylindrical lower portion 116 may have an internal thread which mates with a corresponding thread of a bone fastener. In the present embodiment as shown in FIGS. 17a to 19a the first bone attachment member has four through holes 106. However, one, two or more (e.g., more than four) through holes 106 may be provided in the bone attachment portion 104 of the first bone attachment member 102.

FIG. 17b shows a perspective view of a second bone attachment member 120 according to a first embodiment. FIG. 18b shows a bottom view of the second bone attachment member 120 of FIG. 17b and FIG. 19b shows a cross section of the second bone attachment member 120 along line G-G of FIG. 18b. The second bone attachment member 120 is generally configured as the first bone attachment member 102 as described above with reference to FIGS. 17a to 19a and hereinafter. The difference between the second bone attachment member 120 and the first bone attachment member 102 is that the second bone attachment member 120 has another orientation as the first bone attachment member 102. Thus, the first bone attachment member 102 is adapted to be releasably coupled to the base 12 and the second bone attachment member 120 is adapted to be releasably coupled to the carrier 14. The first and second bone attachment members 102 and 120 may be made of a bio-resorbable material. Alternatively, the first and second bone attachment members 102, 120 may be made of a bio-compatible material, such as stainless steel, titanium or any alloy thereof.

Figure 20:
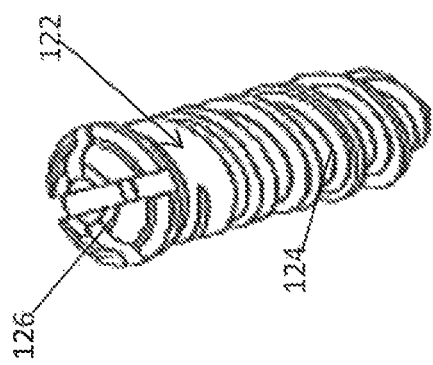
FIG. 20 shows a perspective view of a bone screw.

FIG. 20 shows a perspective view of a bone fastener 122. The bone fastener 122 is in the present embodiment a bone screw. The bone fastener 122 has a threaded shaft 124 and a head 126. The head 126 of the bone fastener 122 is adapted to be seated on the countersink upper portion 118 of each of the through holes 106 of the first or second bone attachment member 102, 120. The bone fastener 122 is made of a resorbable or non-resorbable material. Thus, the bone fastener 122 can be made of a bio-resorbable material or any type of stainless steel, titanium or any alloy thereof. In practice, one or more, e.g., four, bone fasteners 122 will be provided for attaching the bone attachment members 102, 120, and thus the surgical distance adjusting assembly 10, to bone.

Figure 21:
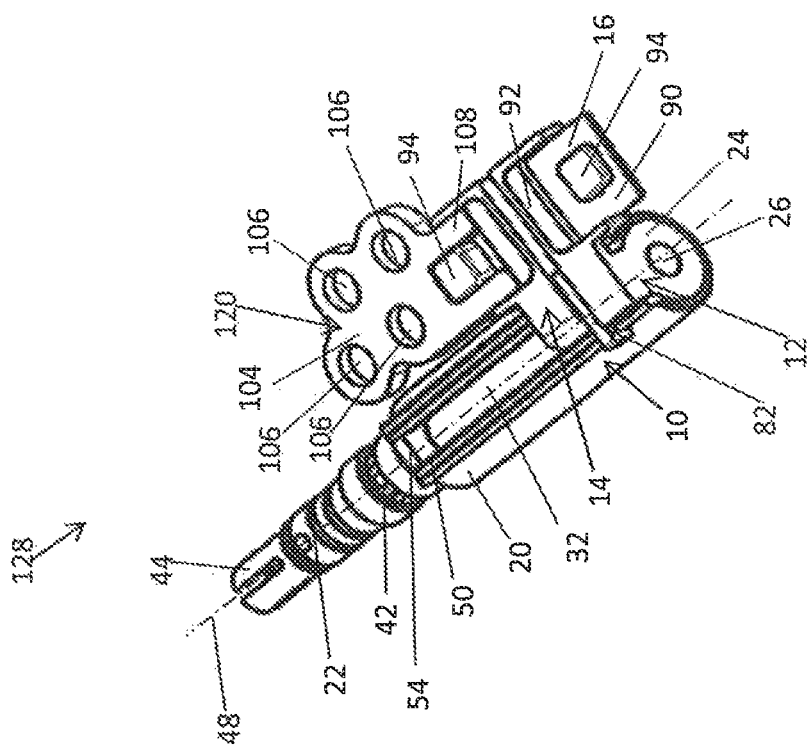
FIG. 21 shows a bone distractor comprising the adjusting assembly of FIG. 1 and the second bone attachment member of FIG. 17*b*.

FIG. 21 shows a bone distractor 128 comprising the surgical distance adjusting assembly 10 and the first and second bone attachment members 102, 120 (only one bone attachment member is shown). Here, it can be seen that the first and second connecting portions 16, 18 of the base 12 and the carrier 14 respectively are oriented in a direction of the longitudinal axis 48 of the adjusting assembly 10. Further, the engagement cavities 90 of the first and second connecting portions 16, 18 open out in a direction of the longitudinal axis 48 of the adjusting assembly 10. As shown in FIG. 21, the engagement cavities 90 open out in opposite directions. Thus, one engagement cavity 90 opens out towards one end of the bone disctractor 128 and the other engagement cavity 90 opens out towards the other end of the bone distractor 128. Hence, the first and second connecting portions 16, 18 point in opposite directions. The base 12 and the carrier 14 and therewith the first and second bone attachment members 102 and 120 move in opposite directions along a line parallel to the longitudinal axis 48 of the adjusting assembly 10 upon rotation of the rotation transmitting member 22. The bone distractor 128 can therefore be distracted from its most reduced configuration as shown in FIG. 21 to its most distracted configuration. Thus, a large spread between the first bone attachment member 102 and the second bone attachment member 120 in relation to the size of the bone distractor 128 can be obtained.

As shown in FIG. 21, the first bone attachment member 102 is releasably coupled to the first connecting portion 16 of the base 12 and the second bone attachment member 120 is releasably coupled to the second connecting portion 18 of carrier 14 (only the latter is shown). During explantation of the adjusting assembly 10, the rotation transmitting member 22 is driven, such that the carrier 14 and the base 12 move towards each other. Upon moving of the carrier 14 and the base 12 towards each other in a direction of the longitudinal axis 48 of the adjusting assembly 10, the adjusting assembly 10 of the bone distractor 128 releases the first and a second bone attachment members 102, 120 from the first and second connecting portions 16, 18. Thus, upon moving of the carrier 14 and the base 12 towards each other (i.e., from a distracted configuration to a reduced configuration of the bone distractor 128), the hook members 94 of the first and second connecting portions 16, 18 slide out of the engagement portions 112. Then, the hook members 94 can be released out of the recesses 110.

Figure 22:
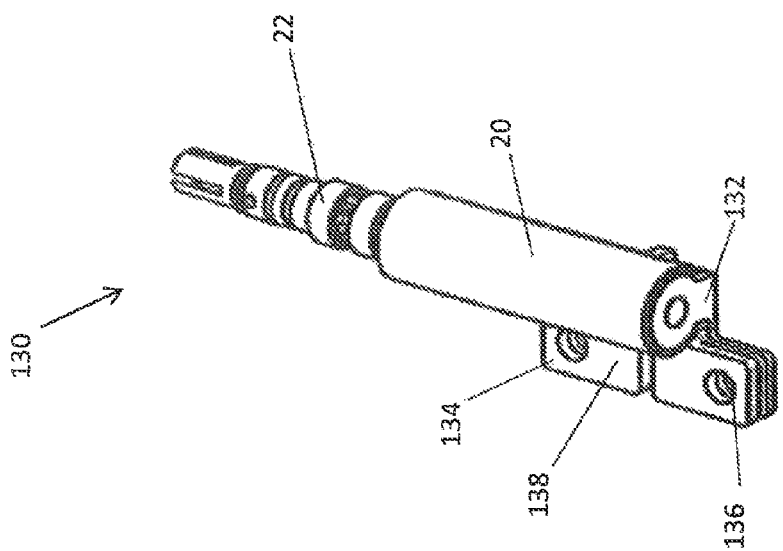
FIG. 22 shows a perspective view of a surgical distance adjusting assembly ac-cording to a second embodiment in its most reduced configuration.

FIG. 22 shows a perspective view of a further embodiment of a surgical distance adjusting assembly 130. In this view, the surgical distance adjusting assembly 130 is in its most reduced configuration. The surgical distance adjusting assembly 130 is now referred to as an adjusting assembly 130. The adjusting assembly 130 comprises a base 132 and a carrier 134. The base 132 has a first connecting portion 136 according to a second embodiment which is configured to hold a first bone attachment member according to a second embodiment (not shown in FIG. 1). The carrier 134 has a second connecting portion 138 according to a second embodiment which is configured to hold a second bone attachment member according to a second embodiment (not shown in FIG. 1). Further, the adjusting assembly 130 comprises the rod cover 20 and the rotation transmitting member 22.

Figure 23:
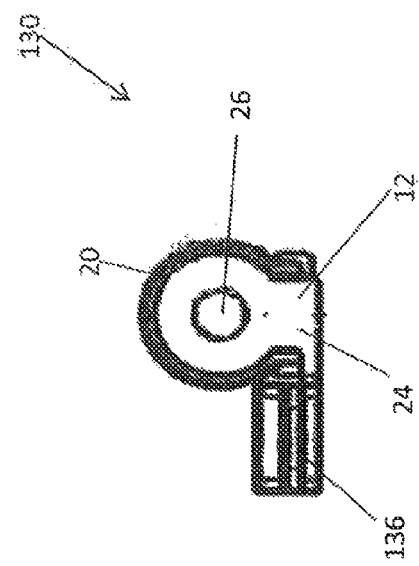
FIG. 23 shows a rear view of the bone adjusting assembly of FIG. 22.

FIG. 23 shows a rear view of the adjusting assembly 130 of FIG. 22. Here, the base 12 comprising the rod cover 22 and the first connecting portion 136 can be seen. The base 12 has the flat outer surface 24 and the central portion with the cylindrical clearance. The rod 26 is rigidly fixed to the base 12 at the central portion within the cylindrical clearance.

The adjusting assembly 130 includes the rod cover 20, the rod 26, the sleeve 32, the sleeve cover 50 and the rotation transmitting member 22 as generally described above with reference to the adjusting assembly 10, FIGS. 1 to 10 and hereinafter. Thus, the adjusting assembly 130 according to the second embodiment is generally configured as the adjusting assembly 10 described above with reference to FIGS. 1 to 10 and hereinafter. The difference between the adjusting assembly 130 and the adjusting assembly 10 is that the adjusting assembly 130 includes a base 132 and a carrier 134 with first and second connecting portions 136, 138 according to a second embodiment.

Figure 24:
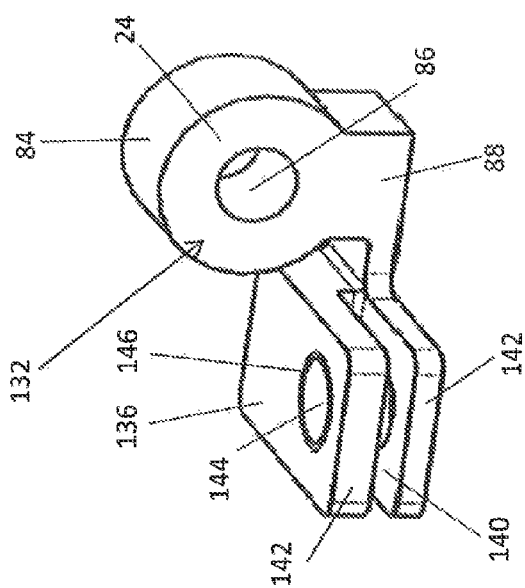
FIG. 24 shows a perspective view of a base according to a second embodiment.

FIG. 24 shows a perspective view of the base 132 according to a second embodiment. The base 132 comprises the cylindrical portion 84 with the cylindrical clearance 86 as generally described above with reference to FIGS. 11 to 13 of the base 12 according to the first embodiment. The rod 26 is thus rigidly fixed to the base 132 at the center of the cylindrical portion 84 within the cylindrical clearance 86. Further, the base 132 has the cuboid 88 as described above with reference to the base 12 according to the first embodiment. The cuboid 88 with the rectangular base extends radially from the cylindrical portion 84 of base 132. In FIG. 24, it can be seen that the outer counter of cylindrical portion 84 of the base 132 corresponds to the inner surface of the rod cover 20.

Figure 25:
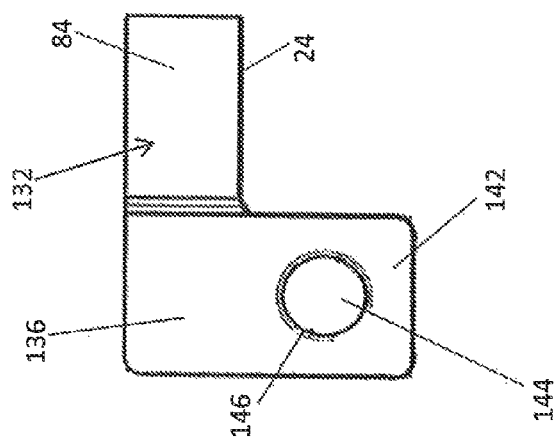
FIG. 25 shows a top view of the base of FIG. 24.

FIG. 25 shows a top view of the base 132 of FIG. 24. The base 132 comprises the first connecting portion 136 which substantially extends in a perpendicular direction with respect to the longitudinal axis of the cylindrical portion 84 of the base 132. Thus, the first connecting portion 136 of the base 132 substantially extends in a perpendicular direction with respect to the longitudinal axis 48 of the adjusting assembly 130, as generally described above with reference to FIGS. 1 to 10 according to the first embodiment. In an equal manner as the base 12 and its first connecting portion 16, the base 132 and its first connecting portion 136 are formed from one single piece of material, e.g., metal.

Figure 26:
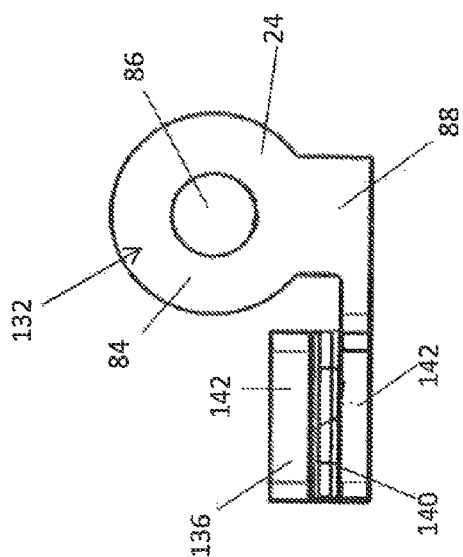
FIG. 26 shows a rear view of the base of FIG. 24.

FIG. 26 shows a rear view of the base 132 of FIG. 24. As shown in FIGS. 24 and 26, the first connecting portion 136 of the base 132 comprises a portion with a recess 140 which is formed as a slit. The recess 140 is configured to slidably receive a bone attachment member (not shown in FIGS. 24 to 26). The recess 140 may have a substantially rectangular shape. The recess portion of the first connecting portion 136 substantially extends in a parallel direction with respect to the longitudinal axis of the cylindrical portion 84 of the base 132. Thus, the recess portion of the first connecting portion 136 substantially extends in a parallel direction with respect to the longitudinal axis 48 of the adjusting assembly 130. The recess 140 may have an U-shape. The recess 140 substantially corresponds to the shape of an assembly connecting portion of the bone attachment members as will be described later in more detail.

As shown in FIGS. 24 and 26, the recess 140 of the first connecting portion 136 opens out in a direction of a longitudinal axis of the cylindrical portion 84 of the base 132. In this case, the recess 140 opens out in the direction of the longitudinal axis 48 of the adjusting assembly 130. The recess 140 is formed by two wings 142 of the first connecting portion 136. The two wings 142 are parallel and opposite to each other as shown in FIGS. 24 and 26. Further, the recess 140 of the first connecting portion 136 also opens out in a direction substantially perpendicular to the longitudinal axis of the adjusting assembly 130. Alternatively, the first connecting portion 136 is formed as a plate portion, for example formed by one (a single) wing. In this case, the first connection portion 136 may have no recess.

Further, as shown in FIGS. 24 to 26, the first connecting portion 136 includes an opening 144 in form of a through hole 144. The through hole 144 penetrates the recess 140. Moreover, the through hole 144 is configured to receive a fixation member in form of a fixation screw for releasably coupling a bone attachment member to the first connecting portion 136 of base 132. The through hole 144 penetrates the first connecting portion 136 and the recess 140 in a direction substantially perpendicular to the longitudinal axis 48 of the adjusting assembly 130. In other words, each wing 142 of the first connecting portion 136 includes a through hole 144, wherein the through holes 144 of the wings 142 coincide with each other. Alternatively, the through hole 144 penetrates the plate portion of the first connecting portion 136. The through hole 144 further has an internal thread 146 which mates with an external thread of a corresponding fixation screw. The internal thread 146 of the through hole may be, as in the present embodiment, a machine thread. The through hole 144 may be circular as shown in FIGS. 24 and 25 or can have an elongated shape, i.e., can be an elongated through hole.

Figure 27:
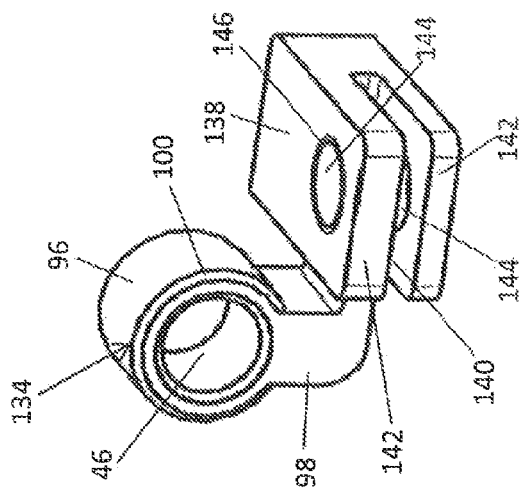
FIG. 27 shows a perspective view of a carrier according to a second embodiment.

FIG. 27 shows a perspective view of the carrier 134 according to a second embodiment. The carrier 134 is generally configured as the carrier 14 described with reference to FIGS. 14 to 16 and hereinafter. The difference between the carrier 134 according to the second embodiment and the carrier 14 according to the first embodiment is that the carrier 134 comprises the second connecting portion 138 according to a second embodiment. Thus, carrier 134 comprises the cylindrical portion 96 in which the internal thread 46 is provided. Further, the carrier 134 has the cuboid 98 with the rectangular base which extends radially from the cylindrical portion 96. It can be seen in FIG. 27, that the outer contour of the carrier 134 (i.e., of its cylindrical portion 96) corresponds to the inner surface of the sleeve cover 50 (see FIGS. 9, 10 and 23). The cylindrical portion 96 has at its end portions in the longitudinal direction of the cylindrical portion 96 the chamfered portion 100. The chamfered portions 100 extend substantially along the outer circumference of the cylindrical portion 96.

Figure 29:
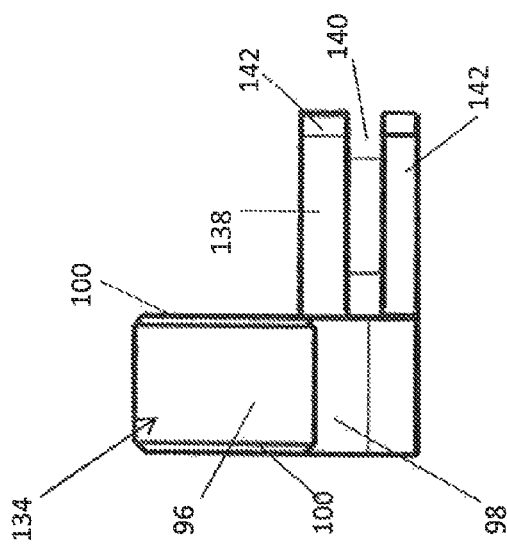
FIG. 29 shows a front view of the carrier of FIG. 27.
Figure 28:
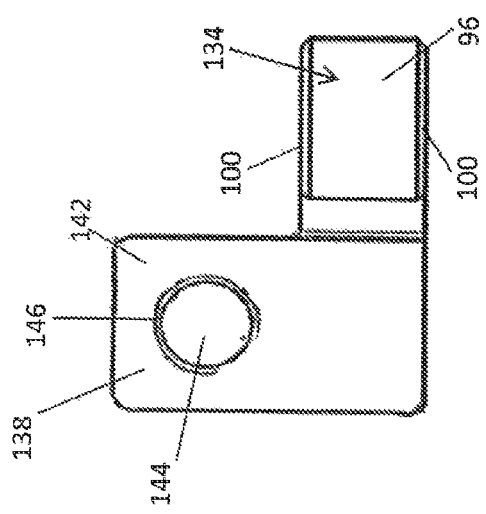
FIG. 28 shows a top view of the carrier of FIG. 27.

FIG. 28 shows a top view of the carrier 134 of FIG. 27 and FIG. 29 shows a front view of the carrier 134 of FIG. 27. As can be seen from FIGS. 27 to 29, the carrier 134 further comprises the second connecting portion 138. The second connecting portion 138 is configured to hold a second bone attachment member (not shown in FIGS. 27 to 29). The second connecting portion 138 provides a releaseable mechanical coupling to the second bone attachment member. The second connecting portion 138 of the carrier 134 substantially corresponds to the first connecting portion 136 of base 132. Thus, the second connecting portion 138 includes the recess 140, the two wings 142 and the through hole 144 as generally described above with reference to FIGS. 24 to 26 and hereinafter. Alternatively, as described above with reference to the first connecting portion 136 of base 132, the second connecting portion 138 of carrier 134 can be formed as a plate portion including the through hole 144.

FIG. 30a shows a perspective view of a first bone attachment member 148 according to a second embodiment. The first bone attachment member 148 is generally configured as the first bone attachment member 102 described with reference to FIGS. 17a to 19a. Thus, the first bone attachment member 148 has the bone attachment portion 104 including the through holes 106 as generally configured and described above with reference to FIGS. 17a to 19a. The bone attachment member 148 can also have several shapes which can be adapted as needed to the structure of the adjusting assembly 130 or to the bone structure. The first bone attachment member 148 further comprises an assembly connecting portion 150 according to a second embodiment. The assembly connecting portion 150 has a substantially rectangular shape and is the counter-part of the first and second connecting portions 136 and 138 of the base 132 and the carrier 134 respectively.

FIG. 31a shows a top view of the first bone attachment member of FIG. 30a and FIG. 32a shows a cross section of the first bone attachment member 148 along line I-I of FIG. 31a. It can be seen from FIGS. 30a to 32a, that the assembly connecting portion 150 of the first bone attachment member 148 includes an opening 152 in form of a through hole 152. The through hole 152 has a central position with respect to the rectangular assembly connecting portion 150. The through hole 152 can be, as in the present embodiment, a circular hole or an elongated hole. The through hole 152 may further be generally configured as the through hole 144 of the base 132 or the carrier 134. Thus, the through hole 152 may be threaded or unthreaded. In the present embodiment, the through hole 152 is an unthreaded circular through hole. When the first bone attachment member 148 is coupled to the first connecting portion 136 of base 132, the through hole 152 of the first bone attachment member 148 coincides with the through hole 144 of the first connecting portion 136 of base 132. In this case, the assembly connecting portion 150 matingly fits within the recess 140 of base 132. Thus, the fixation member may penetrate the through hole 144 of the first connecting portion 136 and the through hole 152 of the first bone attachment member 148. As shown in FIG. 32a, the assembly connecting portion 150 may be formed as a step portion which can be accommodated with recess 140 of base 132. In this case, the assembly connecting portion 150 has a thickness smaller than a thickness of the bone attachment portion 104.

FIG. 30b shows a perspective view of a second bone attachment member 154 according to a second embodiment. FIG. 31b shows a top view of the second bone attachment member 154 of FIG. 30b and FIG. 32b shows a cross section of the second bone attachment member 154 along line J-J of FIG. 31b. The second bone attachment member 154 is generally configured as the first bone attachment member 148 as described above with reference to FIGS. 30a to 32a and hereinafter. The difference between the second bone attachment member 154 and the first bone attachment member 148 is that the second bone attachment member 154 has another orientation as the first bone attachment member 148. Thus, the first bone attachment member 148 is adapted to be releasably coupled to the base 132 and the second bone attachment member 154 is adapted to be releasably coupled to the carrier 134. The first and second bone attachment members 148 and 154 may be made of a bio-resorbable material. Alternatively, the first and second bone attachment members 148, 154 may be made of a bio-compatible material, such as stainless steel, titanium, or any alloy thereof.

Figure 33:
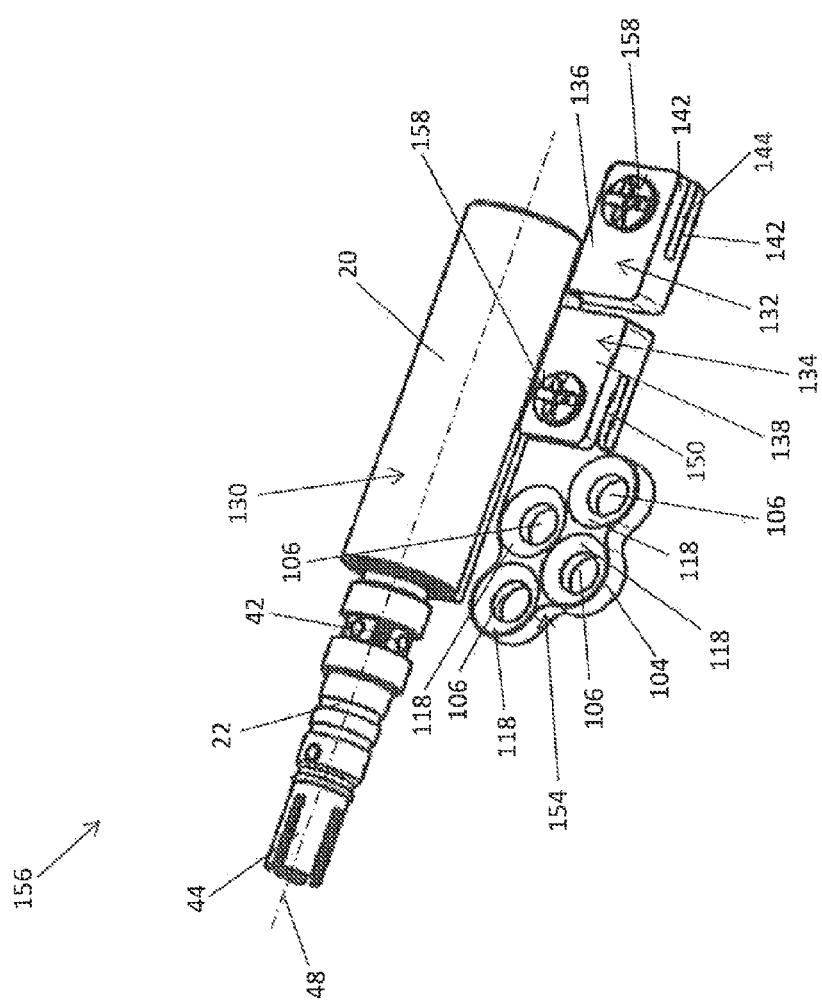
FIG. 33 shows a bone distractor comprising the adjusting assembly of FIG. 22 and the second bone attachment member of FIG. 30b.

FIG. 33 shows a bone distractor 156 comprising the surgical distance adjusting assembly 130 and the first and second bone attachment members 148, 154 (only one bone attachment member is shown). Here, it can be seen that the first and second connecting portions 136, 138 of the base 132 and the carrier 134 respectively are oriented in a direction of the longitudinal axis 48 of the adjusting assembly 130. Further, the recess 144 of the first and second connecting portions 136, 138 opens out in a direction of a longitudinal axis 48 of the adjusting assembly 130. As shown in FIG. 33, the recesses 144 open out in opposite directions. Thus, one recess 144 opens out towards one end of the bone distractor 156 and the other recess 144 opens out towards the other end of the bone distractor 156. Hence, the first and second connecting portions 136, 138 point in opposite directions. The base 132 and the carrier 134 and therewith the first and second bone attachment members 148 and 154 move in opposite directions along a line parallel to the longitudinal axis 48 of the adjusting assembly 130 upon rotation of the rotation transmitting member 22. The bone distractor 156 can therefore be distracted from its most reduced configuration as shown in FIG. 33 to its most distracted configuration. Thus, a large spread between the first bone attachment member 148 and the second bone attachment member 154 in relation to the size of the bone distractor 156 can be obtained.

As further shown in FIG. 33, the through holes 152 of the first and second bone attachment members 148, 154 coincide with the corresponding through hole 144 of the first and second connecting portion 136, 138 respectively, when the first and second bone attachment members 148, 154 are coupled to the first and second connecting portions 136, 138. Moreover, each bone attachment member 148, 154 is fixed to the corresponding base 132 and carrier 134 respectively with a fixation screw 158. Each fixation screw 158 penetrates the through hole 144 of one of the first and second connecting portions 136, 138 and the through hole 152 of the corresponding first and second bone attachment member 148, 154. The fixation screw 158 can be, as in the present embodiment, a fastener in form of a machine screw having a machine thread. Alternatively, the fixation screw 158 can be a peg, pin or the like. The fixation screw 158 may have an external thread which mates with the internal thread 146 of the through hole 144 of the first and second connecting portions 136, 138. Further, the fixation screw 158 has a shaft with the external thread. The shaft of the fixation screw 158 has a length that equals to or is smaller than an total thickness (or total height) of the connection portion 136, 138 of base 132 or carrier 134 and the assembly connecting portion 150 of bone attachment member 148, 154.

The first and second bone attachment members 148, 154 can be attached to bone by the bone fastener 122 as described above with reference to FIG. 20. In practice, one or more, e.g., four, bone fasteners 122 will be provided for attaching the bone attachment members 148, 154, and thus the surgical distance adjusting assembly 130, to bone.

As shown in FIG. 33, the first bone engagement member 148 is releasably coupled to the first connecting portion 136 of the base 132 and the second bone engagement member 154 is releasably coupled to the second connecting portion 138 of the carrier 134 (only the latter is shown). During explanation of the adjusting assembly 130, the fixation members 158 have firstly been removed, e.g., by a tool like a screw driver. Thereafter, the rotation transmitting member 22 is driven, such that the carrier 134 and base 132 move toward each other. Upon moving of the carrier 134 and the base 132 towards each other in the direction of the longitudinal axis 48 of the adjusting assembly 130, the adjusting assembly 130 of the bone distractor 156 releases the first and second bone attachment members 148, 154 from the first and second connecting portions 136, 138. Thus, upon moving of the carrier 134 and the base 132 towards each other (i.e., from a distracted configured to a reduced configuration of the bone distractor 156), the assembly connecting portions 150 of the first and second bone attachment member 148, 154 slide out of the recesses 144.

During surgery, the bone distractor 128, 156 is inserted through a skin incision towards a bone structure of a patient (e.g., in a mandibular region). For example, the bone distractor may be, in an initial configuration, in its most reduced configuration. Then, the first bone attachment member 102, 148 and the second bone attachment member 120, 154 are fixed to bone by bone screws 122. In particular, the first bone attachment member 102, 148 is fixed to a first bone section by bone screws 122 and the second bone attachment member 120, 184 is fixed to another bone section (e.g., a bone section opposite to the bone section on which the first bone attachment member 102, 184 is fixed) by bone screws 122, wherein the two bone sections are separated by a gap.

The bone distractor 128, 156 may then be operated by rotating a wire or any other element connected to the rotation transmitting member 22 through, e.g., the incision in the skin of the patient. By rotating tool interface 44, the sleeve 32, having the internal thread 34 for engaging the thread 46 of the carrier 14, 134, is correspondingly rotated via the rotation transmitting member 22. The sleeve 32 thereby moves along the longitudinal axis 48 relative to the rod 26 away from the base 12, 132 holding the first bone attachment member 102, 148. Upon rotation of the sleeve 32, the carrier 14, 134, holding the second bone attachment member 120, 154 and rotationally locked relative to the sleeve cover 50, moves along the longitudinal axis 48 relative to the sleeve 32 away from the base 12, 132. For one given rotational speed of the sleeve 32, the carrier 14, 134 may move faster relative to the rod 26 than the sleeve 32 moves relative to the rod 26 along the longitudinal axis 48.

Thus, by rotation of the sleeve 32, the base 12, 132 and the carrier 14, 134 move in opposite directions in relation to the sleeve 32 along the longitudinal axis 48. Consequently, the first and second bone attachment members 102, 148 and 120, 154 (and the associated bone sections) are successively distracted. The successive separation of the bone sections causes new bone to form in the generated gap, wherein the bone distractor 128, 156 may temporarily maintain a fixed gap width. After a consolidation phase of bone, the bone distractor 128, 156 is removed, e.g., with or without the first and the second bone attachment members 102, 148 and 120, 154, as generally described above with reference to FIGS. 21 and 33 respectively. In this case, the fixation screws 158 are firstly removed to release the first and second bone attachment members 148, 154 from the first and second connection portions 136, 138 (i.e., loosen the releasable mechanical coupling).

Generally, the bone distractor may be made of any material. As an example, the bone distractor 128, 156 may be made from a metal such as titanium or stainless steel. In such a case, the base 12, 132 as well as the carrier 14, 134 may also be made from a bio-compatible metal. The first and second bone attachment members 102, 148 and 120, 154 can be made of a resorbable material, and one or more (or alle) components of the remaining bone distractor 128, 156 (i.e., of the surgical distance adjusting assembly) may be made of a non-resorbable material such as metal (e.g., titanium). In a still further variant, the complete surgical distractor 128, 156, including the first and the second bone attachment members 102, 148 and 120, 154 is made from a resorbable material.

As will be appreciated, the bone distractor 128, 156 as presented herein has a particularly simple structure. The risk of tissue debris adhesion is reduced and a cleaning and sterilization procedure, if needed, of the bone distractor 128, 156 is facilitated.

The configuration of the bone distractor 128, 156 enables it to be manufactured small in size while maintaining the availability of a sufficiently wide range of operating distances between the bone attachment members 102, 148 and 120, 154. Due to its configuration, the bone distractor 128, 156 is maintained compact through all operating distances from the most reduced position to the most distracted position.

While the present disclosure has been described with reference to exemplary embodiments, it will be appreciated that the present disclosure is not limited to what has been described above. It will, for example, be appreciated, that the dimensions of the parts may be varied as needed.

The features described in the above description taken in conjunction with the accompanying drawings can be readily combined to result in different embodiments. For example, the carrier according to the first embodiment shown in FIGS. 14 to 16 could be combined with the base according to the second embodiment shown in FIGS. 24 to 26 (or vice versa) in one surgical distance adjusting assembly, i.e., in one bone distractor.

It will thus be apparent that the present disclosure may be varied in many ways. Such variations are not to be regarded as a departure from the scope of the disclosure, and all modifications are intended to be included within the scope of the following claims.

The invention claimed is:

1. A surgical distance adjusting assembly for a bone distractor, the assembly comprising:
    a base having a first connecting portion configured to hold a first bone attachment member;
    a carrier having a second connecting portion configured to hold a second bone attachment member, the base and the carrier being movable along a longitudinal axis relative to each other and the first and second connecting portions providing a releasable mechanical coupling to the first and second bone attachment members; and
    wherein the releasable mechanical coupling comprises a hook member at one or both of the first and second connecting portions to engage a cavity, the cavity is configured to at least partially receive the hook member of the respective connecting portion by movement in a direction perpendicular to the longitudinal axis of the base and carrier, and maintain the respective hook members within the cavity during the relative axial movement of the first and second connecting portions.

2. The surgical distance adjusting assembly according to claim 1, wherein one or both of the first and second connecting portions comprises an engagement surface configured to slidably abut against the respective bone attachment member.

3. The surgical distance adjusting assembly according to claim 1, wherein the engagement surface delimits an engagement cavity of the respective connecting portion.

4. The surgical distance adjusting assembly according to claim 3, wherein the hook member is arranged within the engagement cavity.

5. The surgical distance adjusting assembly according to claim 3, wherein the engagement cavity or the recess opens out in a direction of a longitudinal axis of the surgical distance adjusting assembly.

6. The surgical distance adjusting assembly according to claim 3, wherein the engagement cavity or the recess opens out in opposite directions along a direction of a longitudinal axis of the surgical distance adjusting assembly.

7. The surgical distance adjusting assembly according to claim 1, wherein the surgical distance adjusting assembly is configured to release, upon a movement of the carrier and the base towards each other in a direction of a longitudinal axis of the surgical distance adjusting assembly, the first and second bone attachment members from the first and second connecting portions.

8. The surgical distance adjusting assembly according to claim 1, wherein the carrier is rotationally locked relative to the base.

9. A surgical distance adjusting assembly for a bone distractor, the assembly comprising:
    a base having a first connecting portion configured to hold a first bone attachment member; and
    a carrier having a second connecting portion configured to hold a second bone attachment member, the base and the carrier being movable relative to each other along a longitudinal axis and the first and second connecting portions providing a releasable mechanical coupling to the first and second bone attachment members,
    wherein the releasable mechanical coupling comprises a hook member at one or both of the first and second connecting portions to engage the respective bone attachment member, and
    wherein one or both of the first and second connecting portions comprises an engagement cavity, wherein the hook member is placed within the respective engagement cavity by movement in a direction perpendicular to the longitudinal axis and maintained therein during axial movement of the respective connecting portion.

10. The surgical distance adjusting assembly according to claim 9, wherein one or both of the first and second connecting portions comprises an engagement surface configured to slidably abut against the respective bone attachment member.

11. The surgical distance adjusting assembly according to claim 9, wherein the engagement surface delimits the engagement cavity of the respective connecting portion.

12. The surgical distance adjusting assembly according to claim 9 wherein the hook member extends in a substantially parallel direction of a longitudinal axis of the surgical distance adjusting assembly.

13. The surgical distance adjusting assembly according to claim 9 wherein the engagement cavity has a longitudinal axis extending parallel to the longitudinal axis of the surgical distance adjusting assembly.

14. The surgical distance adjusting assembly according to claim 9 wherein the engagement cavity of the first connecting portion opens out towards a first end of the surgical distance adjusting assembly, and the engagement cavity of the second connecting portion opens out towards a second end of the surgical distance adjusting assembly.

15. The surgical distance adjusting assembly according to claim 9 wherein the engagement cavity is adapted to a shape of an assembly connecting portion of the respective bone attachment member to provide a substantially matching fit therebetween.

16. The surgical distance adjusting assembly according to claim 9 wherein each of the first and second connecting portions comprises more than one hook members configured to releasable engage an engagement portion of the respective bone attachment member.

17. The surgical distance adjusting assembly according to claim 9 wherein the surgical distance adjusting assembly is configured to release the first and second bone attachment members from the first and second connecting portions upon a movement of the carrier and the base towards each other in a direction of the longitudinal axis.

18. The surgical distance adjusting assembly according to claim 9 wherein the carrier is rotationally locked against rotation relative to the base.

19. A surgical distance adjusting assembly for a bone distractor, the assembly comprising:
a base having a first connecting portion configured to releasably hold a first bone attachment member to the base;
a carrier mounted on the base and moveable with respect thereto, the carrier having a second connecting portion configured to releasably hold a second bone attachment member to the carrier, the base and the carrier being movable relative to each other along a longitudinal axis and the first and second connecting portions providing a releasable mechanical coupling to the first and second bone attachment members, and wherein the mechanical coupling maintains the first and second attachment members in a fixed position with respect to the base and the carrier during the relative axial movement of the base and carrier, the first and second attachment members mountable on a bone surface; and
the connecting portions of the base and carrier and the first and second attachment members have a mating hook and opening for selectively forming the mechanical coupling between the base and first attachment member and the carrier and the second attachment member, the opening surrounded by portions of the first and second bone attachment members such that the hook is located under a portion of the bone attachment member in a first axial position and located only in the opening in a second axial position, so that release of the first and second attachment members from the base and carrier first requires movement in an axial direction and then in a direction away from the bone surface and perpendicular to the longitudinal axis of the base and carrier.

20. A surgical distance adjusting assembly for a bone distractor, the assembly comprising:
a base having a first connecting portion configured to hold a first bone attachment member;
a carrier having a second connecting portion configured to hold a second bone attachment member, the base and the carrier being movable along a longitudinal axis relative to each other and the first and second connecting portions providing a releasable mechanical coupling to the first and second bone attachment members; and
wherein the releasable mechanical coupling comprises a hook member at one or both of the first and second connecting portions to engage a cavity, the cavity is configured to at least partially receive the hook member of the respective connecting portion and maintain the respective hook members within the cavity during any relative axial movement of the first and second connecting portions along the longitudinal axis, the cavity being configured to at least partially and slidably receive the respective bone attachment member.

* * * * *